United States Patent [19]
Backhaus et al.

[11] Patent Number: 5,535,743
[45] Date of Patent: Jul. 16, 1996

[54] DEVICE FOR THE IN VIVO DETERMINATION OF AN OPTICAL PROPERTY OF THE AQUEOUS HUMOUR OF THE EYE

[75] Inventors: Jurgen Backhaus, Edingen-Neckarhausen; Dirk Bocker, Heidelberg; Bernhard Schrader, Essen; Wolfgang Schrader, Kirchzarten-Burg; Hans-Ulrich Menzebach, Essen; Elmar Schmidt, Mannheim, all of Germany

[73] Assignee: Boehringer Mannheim GmbH, Mannheim, Germany

[21] Appl. No.: 168,195

[22] Filed: Dec. 17, 1993

[30] Foreign Application Priority Data

Dec. 19, 1992 [DE] Germany .......................... 42 43 142.5

[51] Int. Cl.$^6$ ...................................... A61B 5/00
[52] U.S. Cl. ............................. 128/633; 128/664
[58] Field of Search ...................... 128/645, 664, 128/665, 632, 633; 606/2, 4, 13, 17, 18; 600/26–28; 356/39–42

[56] References Cited

U.S. PATENT DOCUMENTS

| | | |
|---|---|---|
| 3,958,560 | 5/1976 | March . |
| 3,963,019 | 6/1976 | Quandt . |
| 4,014,321 | 3/1977 | March . |
| 4,852,987 | 8/1989 | Lohman ................. 128/633 X |
| 5,203,328 | 4/1993 | Samuels et al. ............ 128/633 |
| 5,219,400 | 6/1993 | Jacot et al. ............... 128/633 |
| 5,242,376 | 9/1993 | Shealy et al. .............. 600/27 |
| 5,258,788 | 11/1993 | Furuya ................. 128/633 X |
| 5,284,149 | 2/1994 | Dhadwal et al. ............ 128/665 |

FOREIGN PATENT DOCUMENTS

| | | |
|---|---|---|
| 0160768 | 5/1984 | European Pat. Off. . |
| 0589191A1 | 3/1994 | European Pat. Off. . |
| 2606991 | 8/1977 | Germany . |
| 343684 | 7/1972 | U.S.S.R. . |
| 1377015 | 2/1988 | U.S.S.R. . |
| WO92/07511 | 5/1992 | WIPO . |

OTHER PUBLICATIONS

Noninvasive optical polarimetric glucose sensing using a true phase measurement technique. In: IEEE Transactions on Biomedical Engineering, USA, vol. 39, No. 7, Jul. 1992, S. 752–6.

Noninvasive Glucose Monitoring of the Aqueous Humor of the Eye: Part I. Measurement of Very Small Optical Rotations. Diabetes Care, vol. 5, No. 3 May–Jun. 1982, pp. 254–258.

*Primary Examiner*—Angela D. Sykes
*Assistant Examiner*—Samuel Gilbert
*Attorney, Agent, or Firm*—Nikaido, Marmelstein, Murray & Oram

[57] ABSTRACT

A device for the in vivo determination of an optical property of the aqueous humor in the anterior chamber of the eye includes a light source to irradiate light along a primary-side light path into the anterior chamber of an eye. A detector is provided, in order to detect light issuing from the anterior chamber along a secondary-side light path. A signal processing unit is provided to determine the optical properties on the basis of the measured signal of the detector. A routine in vivo examination of the aqueous humor of the eye, with minor inconvenience to the patient, can be achieved due to the fact that the device can be easily positioned in front of the eye. The central rays of the primary-side light path and of the secondary-side light path form, with the normals to surface of the cornea bordering the anterior chamber, an angle ($\alpha$, $\beta$) such that the detector detects light reflected from the front interface of the eye lens.

12 Claims, 4 Drawing Sheets

DEVICE FOR THE IN VIVO DETERMINATION OF AN OPTICAL PROPERTY OF THE AQUEOUS HUMOUR OF THE EYE

The invention relates to a device for the in vivo determination of an optical property of the aqueous humour in the anterior chamber of the eye with a light source, in order to irradiate light along a primary-side light path into the anterior chamber, a detector, in order to detect light issuing from the anterior chamber along a secondary-side light path, and a signal processing unit, in order to determine the optical properties on the basis of the measured signal of the detector.

The determination of the optical properties of the aqueous humour of the human eye is important above all for medical-diagnostic purposes. In particular the possibility has already been discussed for a long time of determining the concentration of glucose in the anterior chamber by means of an optical property of the aqueous humour which is dependent on the glucose concentration.

In U.S. Pat. No. 3,958,560 published in 1976 and in U.S. Pat. No. 4,014,321 based on the same original application a device is described by means of which the optical rotation of polarized light during passage through the anterior chamber is determined as a criterion for the glucose concentration contained therein. The light source and the detector are to be incorporated in a contact lens, which is placed on the eye. The light is irradiated from one side of the anterior chamber at a low angle through the cornea, passes through the anterior chamber in a straight line and exits on the other side once again at a low angle through the cornea. The light path is therefore a straight line, which forms in a cross-sectional plane through the anterior chamber a secant with respect to the curvature of the cornea.

The non-invasive in vivo determination of glucose by examination of the aqueous humour has exceptional potential advantages compared with the methods commonly used at the present time for glucose determination, such as those used in particular by diabetics. All glucose analysis systems in practical use at the present time operate invasively, i.e. it is necessary to obtain a blood sample for each analytical procedure. This usually takes place by puncture of the finger tip. Because of the pain associated with the invasive analytical procedure, most diabetics determine their blood glucose levels at relatively long intervals.

From a medical point of view, however, a considerably more frequent analysis would be desirable, if possible several times a day, since only in this way, by accurately proportioned and specific doses of insulin, can the glucose concentration in the blood be kept within the standard range. This in turn is of the highest importance, because any aberration in the glucose status not only involves considerable acute risks, but can also lead to serious secondary effects of the diabetes, for example loss of eyesight. In medical circles there is the conviction that such serious delayed effects of diabetes could be largely prevented by far more frequent and closer monitoring of the blood glucose concentration.

For these reasons there is great interest in a facility for the non-invasive in vivo determination of the blood glucose concentration. Since it is known that the glucose concentration in the anterior chamber of the eye correlates with the glucose concentration in the blood, several attempts have been made to develop and improve the measurement technique described in the above-mentioned US patents, the efforts being concentrated on the improvement of the optical-electronic measurement technique. In the article "Non-invasive optical polarimetric glucose sensing using a true phase measurement technique" by G. L. Coté et al., IEEE Transactions on Biomedical Engineering, 1992, 752 to 756, a summary of this development is given in the introduction with numerous literature references. The previously known systems are however critised in that variations due to fluctuations in the light source or interactions of the optical beam with interfering particles can lead to errors in the case of the measurement systems previously used. A particular optical-electronic arrangement is proposed, in order to eliminate such problems. The latter is also the subject matter of the international patent application WO 92/07511.

Another measuring procedure for detecting the very small optical rotation during the passage of light through the anterior chamber is described in: B. Rabinovitch et al. "Non-invasive glucose monitoring of the aqueous humour of the eye: Part I Measurement of very small optical rotations" Diabetes Care, 1982, 254 to 258.

There are available, on the basis of these and similar papers, extraordinarily efficient signal processing units which are suitable in principle for determining the optical properties of the aqueous humour of the eye with an accuracy sufficient for the above-mentioned diagnostic purposes. It nevertheless seems impossible that the devices known for this purpose could be put to practical use. An extreme miniaturization of the components of transmitter and receiver would be required in order to incorporate them into a contact lens. Even if this were achieved, the insertion and removal of the contact lens would represent an unreasonable inconvenience for the majority of diabetes patients, most of whom are older persons.

It is therefore an object of the invention to provide a device for the in vivo determination of an optical property of the aqueous humour of the eye which is suitable for a routine examination with the smallest possible inconvenience to the patient.

The invention provides a device for the in vivo determination of an optical property of the aqueous humour in the anterior chamber of the eye with a light source, in order to irradiate light along a primary-side light path into the anterior chamber. A detector is provided, in order to detect light issuing from the anterior chamber along a secondary-side light path, and a signal processing unit, in order to determine the optical properties on the basis of the measured signal of the detector. The device can be positioned frontally before the eye and the central rays of the primary-side light path and of the secondary-side light path form with the normals to the surface of the cornea in each case an acute angle, so that the detector detects light which is reflected from the front interface of the eye lens.

In the present invention, therefore, in contrast to the previously known methods, the anterior chamber is not irradiated along a secant of the curvature of the cornea for the measurement of the optical properties of the aqueous humour (in particular the absorption or the optical rotation). Instead use is made of the reflection on an interface of the eye lens at the rear side of the anterior chamber. The signal processing unit may be constructed similarly to those of the known devices, some preferred measures being described in greater detail further on.

A diffusely reflecting interface is provided by the surface of the iris. The diffusely reflected light is however depolarized. Consequently based on the reflection of the iris surface only optical absorption measurement is possible whereas measurement of the optical rotation through the aqueous humour is not possible.

For this reason and also because of the interfering light scatter components caused by diffuse reflection, the specular reflection at an interface in the vicinity of the optical axis of the eye (above the pupil) is detected. Said specular reflection is generated by the boundary of the eye lens facing the anterior chamber. Its intensity depends on the difference of the refractive indices of the media bordering the reflecting interface. Since the refractive index differences are relatively small, the reflected signal is very weak. It may however, despite its relatively small intensity, be analyzed on the basis of the explanations given here in such a way that useful information on the optical properties of the aqueous humour can be obtained.

The reflection on interfaces of the cornea and of the lens is known in ophthalmology. Four reflected images ("Purkinje-Sanson images") of an object situated before the eye (for example a candle flame) may be observed, two of which are reflected from the cornea and two from the lens of the eye. The image on the front face of the cornea is by far the most light-intensive, i.e. the strongest reflection is observable on the front side of the cornea. In relation to said strongest reflex the intensity of the reflection used in the context of the present invention on the front interface of the lens is only about 1%. The reflectance of the front interface of the eye lens comes to less than 0.001. In ophthalmology, the reflections on the above-mentioned interfaces are used to examine the structure of these interfaces themselves, not to determine any properties of a substance penetrated by the light path.

Preferably the device according to the invention serves for the determination of the optical rotation (ORD=optical rotary dispersion) or the optical absorption in the whole optical range (UV=ultraviolet, VIS=visible, NIR=near infrared, MIR=medium infrared and FIR=far infrared). Other optical properties of the aqueous humour, for example circular dichroism, magnetically induced phenomena, the Raman effect and fluorescence may also be determined in the context of the invention.

Decisive advantages can be achieved by means of the measurement principle according to the invention.

The device according to the invention may in a similar manner to customary ophthalmic test instruments be arranged in a defined position before the eye. Neither a contact lens nor any other part touching the eye is required.

The light source, the detector, the optical elements of the light paths and the measurement and analysis electronics of the signal processing unit may be accommodated without difficulty in a hand-held or table-top unit. Extreme miniaturization barely achievable in practice, as in the case of the previously known proposals, is not necessary.

The light path traverses the anterior chamber twice. It is thereby sufficiently long for the measurement of the optical rotation, although the measurement light traverses only the thickness of the anterior chamber. For absorption measurements the shorter optical path length in the anterior chamber is advantageous.

The dependence of the optical path length in the anterior chamber on the adjustment of the light path is far less than with previously known units. In the case of the transmission principle customary to date, a misalignement of a tenth of a millimeter already led, on account of the flat spherical cap shape of the anterior chamber, to a change in the optical path length which critically affected the measuring accuracy. On the other hand good reproducibility can be obtained in the case of the invention with relatively simple adjustment measures.

Interference due to reflection on other interfaces, in particular on the cornea, and scatter by turbidities in the parts of the eye traversed by the light path, is minimized in the present invention. Conversely, very strong interference resulted with the previously known arrangement, mainly due to the fact that the cornea was passed through twice very obliquely on a secant.

It is relatively easy to construct the device of the invention in such a way that independent measurement values may be obtained successively for both eyes. For example the optical unit may be swivelled from a first position before the right eye into a second position before the left eye. The measuring accuracy can be enhanced in this way.

A further increase in the measuring accuracy is possible by constructing the device in such a way that a plurality of different optical properties of the aqueous humour, for example the NIR absorption and the optical rotation, are determined independently of one another and are used as criteria for the same analytical quantity, for example the glucose concentration.

The invention will be explained in detail below by means of exemplifying embodiments shown diagrammatically in the figures, wherein.

Figure 1:
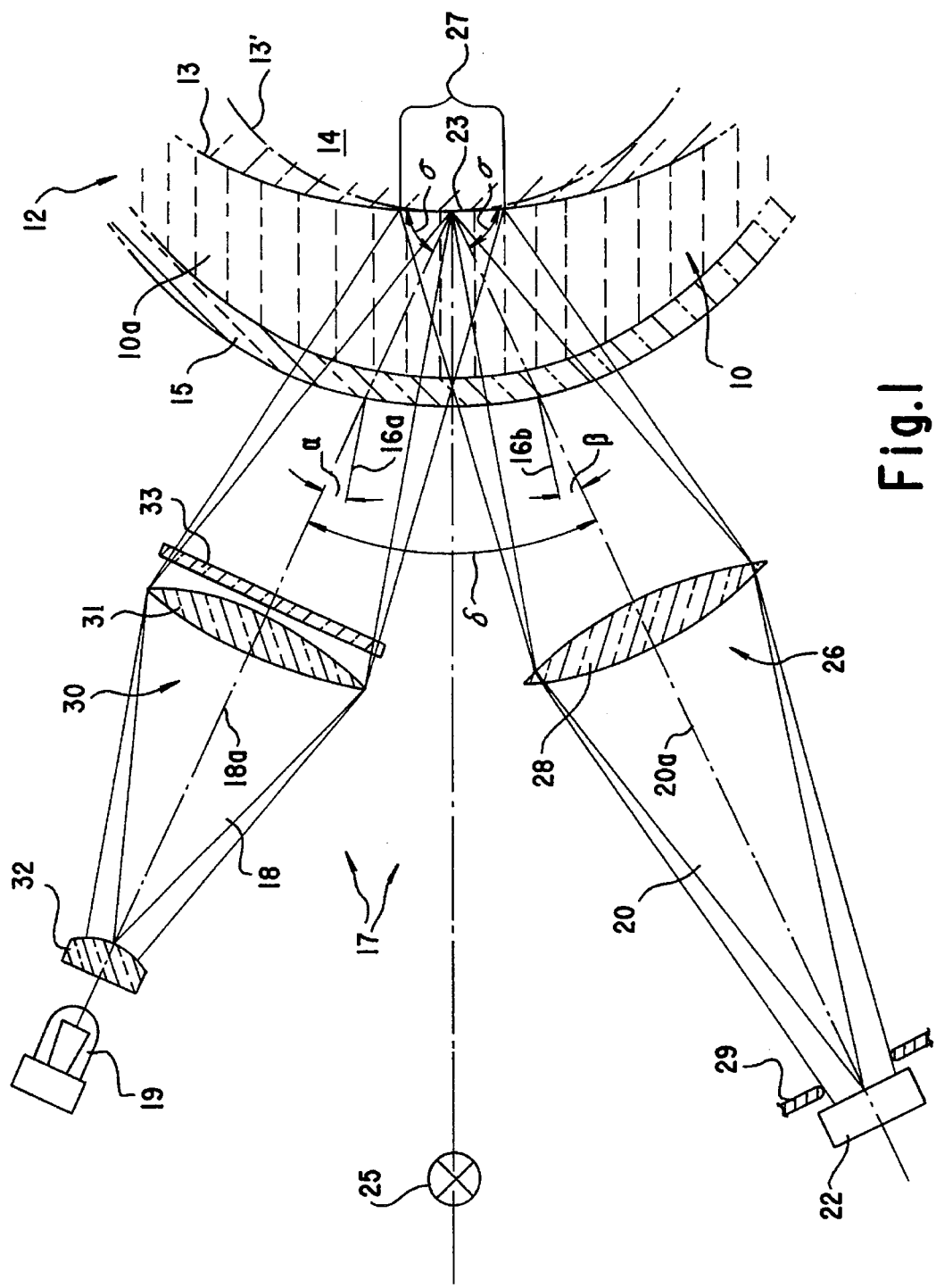
FIG. 1 shows an overall view of a device according to the invention.

FIG. 1 shows, in highly diagrammatic form the anterior chamber 10 of an eye 12. The anterior chamber 10 is bounded towards the interior of the eye by the capsule 13 of the eye lens 14 and towards the outside by the cornea 15.

The optical unit, not drawn to scale and designated overall as 17, of a device for the in vivo determination of an optical property of the aqueous humour 10a contained in the anterior chamber 10 comprises a primary-side light path 18, for irradiating light from a light source 19 into the anterior chamber 10. The light leaving the anterior chamber 10 impinges along a secondary-side light path 20 onto a detector 22.

The primary-side light path 18 and the secondary-side light path 20 may be structured in detail in various ways. FIG. 1 merely shows the features generally necessary or at least advantageous for the invention.

According to the invention the light reflected from an interface 23 on the rear side of the anterior chamber is used for the determination of an optical property of the aqueous humour 10a. The capsula lentis 13 is formed in the region of the front interface 23 of the lens 14 by a thin pellicle. The front and rear side of said pellicle give, jointly with the front side of the lens, a sharp reflex of the incident radiation. This reflex can be used in the context of the invention.

The device is equipped with a fixing light 25 customary in ophthalmic instruments. When the user fixes the fixing light 25, he is led to unfocus to the maximum extent, i.e. the bending of the front capsula lentis 13 reaches its minimum value shown by a solid line in FIG. 1. In comparison the position of the capsula lentis 13' is shown in dashes in the state of maximum focussing (bending radius 5 to 6 mm). In the maximally unfocussed state the front capsula lentis has a bending radius of some 10 mm. The diameter of the pupil amounts to 3 mm with strong central lighting of at least one eye. In the dark the pupil expands to more than 6 mm.

On the basis of the reflection measuring principle used according to the invention the central rays 18a, 20a pass through the cornea 15 virtually at right angles, i.e. the angle α or β between the respective normals 16a, 16b to the outer surface of the cornea 15 (i.e. the normals crossing the cornea at the points where the central rays 18a, 20a respectively cross the outer surface of the cornea) and the central ray 18a, 20a of the light paths 18, 20 is an acute angle of preferably less than 45°, particularly preferably less than 30°. The angle δ between the central rays 18a and 20a may vary within wide limits, greater angles leading to a longer light path within the aqueous humour, which is frequently advantageous, while conversely it may be disadvantageous if the angle at which the cornea is irradiated becomes greater. It is important that the angular arrangement of the light source 19 and the detector 22 should, in any case, be so designed that light components reflected from the interface 23 are detected by the detector 22.

In order to minimize interference by light scatter, the arrangement is preferably so designed that the detector 22 detects the specular reflection issuing from the interface 23. The central rays 18a, 20a of the primary-side light path 18 and of the secondary-side light path 20 impinge on the interface 23 at the same angle σ.

A further reduction in stray light effects can be obtained by using an optical imaging system, for imaging selectively a defined area segment (site) 27 of the interface 23 onto the detector 22. In the embodiment shown the optical imaging system 26 consists of a photographic lens (objective) 28, shown for the sake of simplicity as a simple lens, and a diaphragm 29, which in the preferred case shown is disposed in the region of the image plane, i.e. directly in front of the detector 22. It is naturally also possible to use, instead of the diaphragm, some other means to restrict the illuminated surface of the detector, such as a part of the detector housing.

In order to obtain a sharp reflex with as high an intensity as possible, it may be advantageous to select the form of the surface segment 27 pickled up by the optical imaging system 26 in such a way that its dimension in the plane defined by the central rays 18a, 20a (i.e. in the plane of projection of FIG. 1) is smaller than the dimension perpendicular thereto (i.e. perpendicular to the plane of projection of FIG. 1). In any case the surface segment 27 should be smaller in each dimension than the pupil opening.

In the case of the preferred embodiment shown the primary-side light path 18 also comprises an optical imaging system 30. The latter consists of an objective 31, likewise depicted as a simple lens, and a condensing lens 32 for the light issuing from the light source 19. The objective 31 images the condensing lens 32 onto the reflecting interface 23, so that the defined surface segment 27 of the interface 23 is specifically illuminated. A filter 33 is used to select the desired wavelength of the primary-side light.

In general it is advantageous for the improvement of the signal to noise ratio if not only the secondary-side light path 20 is so designed that a defined surface segment 27 of the reflecting interface 23 is detected but if also the primary-side light path 18 is so formed that as far as possible the same surface segment 27 is specifically illuminated. The illuminated surface may be slightly larger than the surface segment 27, but is in any case smaller than the pupil opening. Instead of the optical imaging system shown this may also be ensured in some other suitable manner. In particular a sharply defined light beam can be provided if a laser is used as a light source, even without a focusing imaging system. Beam widening may be advantageous here in certain circumstances, in order to illuminate a sufficiently large surface segment 27.

A further improvement of the signal to noise ratio may be achieved by directing the primary side light path at the respective Brewster angle to the reflecting surface in which case the reflected light is polarized in a direction perpendicular to the plane of incidence. This increases the reflectivity and allows selection of the reflected light by incorporating a polarizer of the same orientation into the secondary-side light path.

Figure 2:
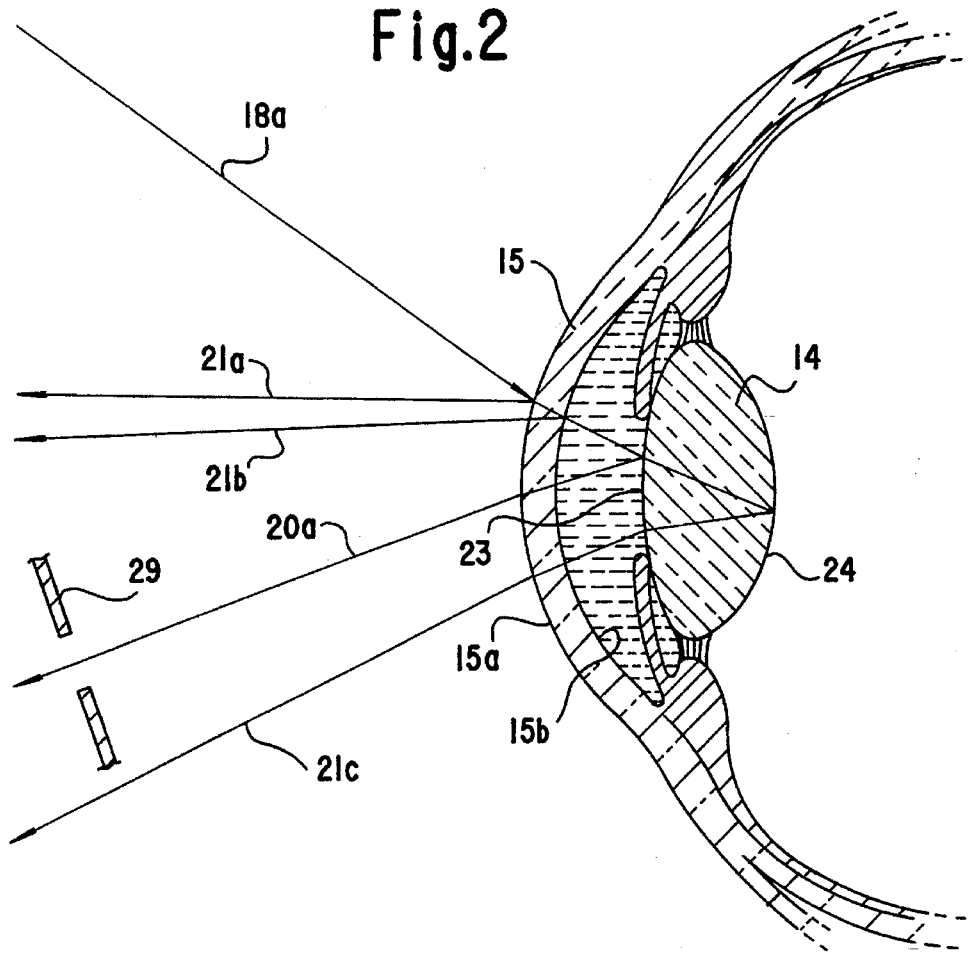
FIG. 2 shows a diagrammatic sectional view of an eye in order to make clear the reflections of various interfaces.

FIG. 2 illustrates the reflection of a primary-side central ray 18a on four interfaces of the eye, namely the front interface 15a and the rear interface 15b of the cornea 15 and also the front interface 23 and the rear interface 24 of the lens 14. The reflection at these interfaces is the cause of the Purkinje-Sanson images mentioned above.

Due to the different angles of incidence on the interfaces the primary-side beam (with the central ray 18a) is reflected in different directions in space. It will be seen that it is possible by means of a merely schematically indicated diaphragm 29 to limit the imaging by the secondary-side beam (with the central ray 20a) to the reflection on the front interface 23 of the lens 14 which is of interest in the context of the present invention.

Figure 3:
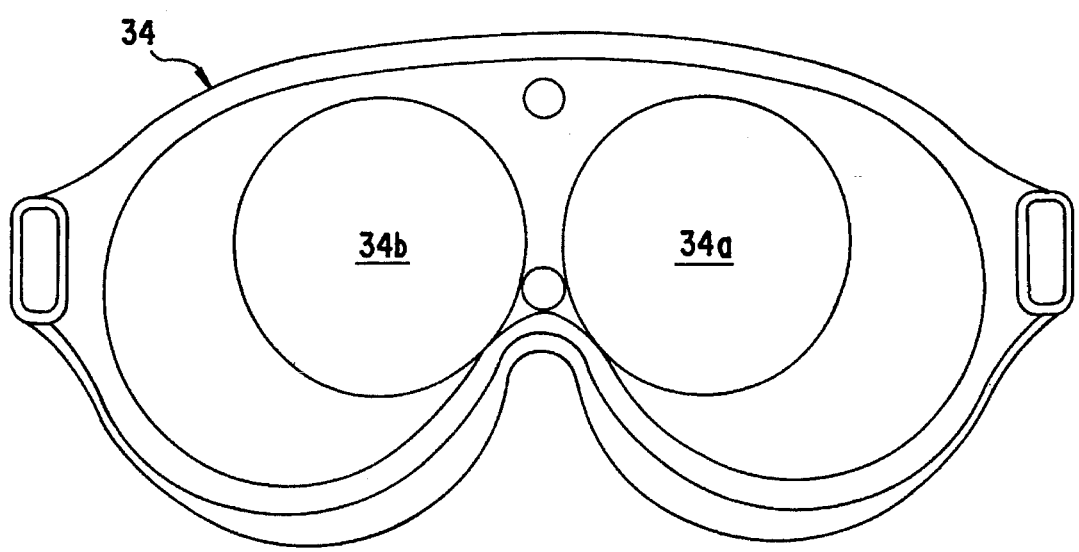
FIG. 3 shows a view from the user's side onto a mask for the defined positioning of a device according to the invention.

FIG. 3 shows a mask 34 for positioning the device according to the invention on the face of the user. It may be constructed in similar fashion to a diving mask or ski goggles, but will be adapted to the respective patient individually, for example by foaming with rigid foam. In the two circular windows 34a and 34b are located opaque diaphragms, which during the adaptation of the device according to the invention are each provided with diaphragm openings adapted to the individual patient for the measuring arrangement with the primary-side light path, the secondary-side light path and the fixing light. The measurement of the optical property takes place with expediency successively for both eyes, the optical unit 17, not represented in FIG. 3, being capable of swivelling, displacement or interchange from one eye to the other. Diaphragm openings not used should be covered in the process.

The embodiment shown in FIG. 1 is suitable in conjunction with a signal processing unit, not shown in the figure but familiar to people of skill in the art, and supplementary customary measures regarding the optical instrument for the determination, for example, of the optical absorption of the aqueous humour 10a. The absorption measurement is usually based on a comparison of the light irradiated into the anterior chamber 10 and the light issuing therefrom. To this end the primary-side light path 18 can comprise a split beam, not shown in FIG. 1, by means of which a reference beam is obtained. The split beam is provided by means of a stationary beam splitter or by means of a mirror projecting temporarily into the primary-side light path 18. A detailed explanation of the absorption measurement is not necessary, because suitable measuring methods are known in the art and may be applied to the present invention without particular problems.

Figure 4:
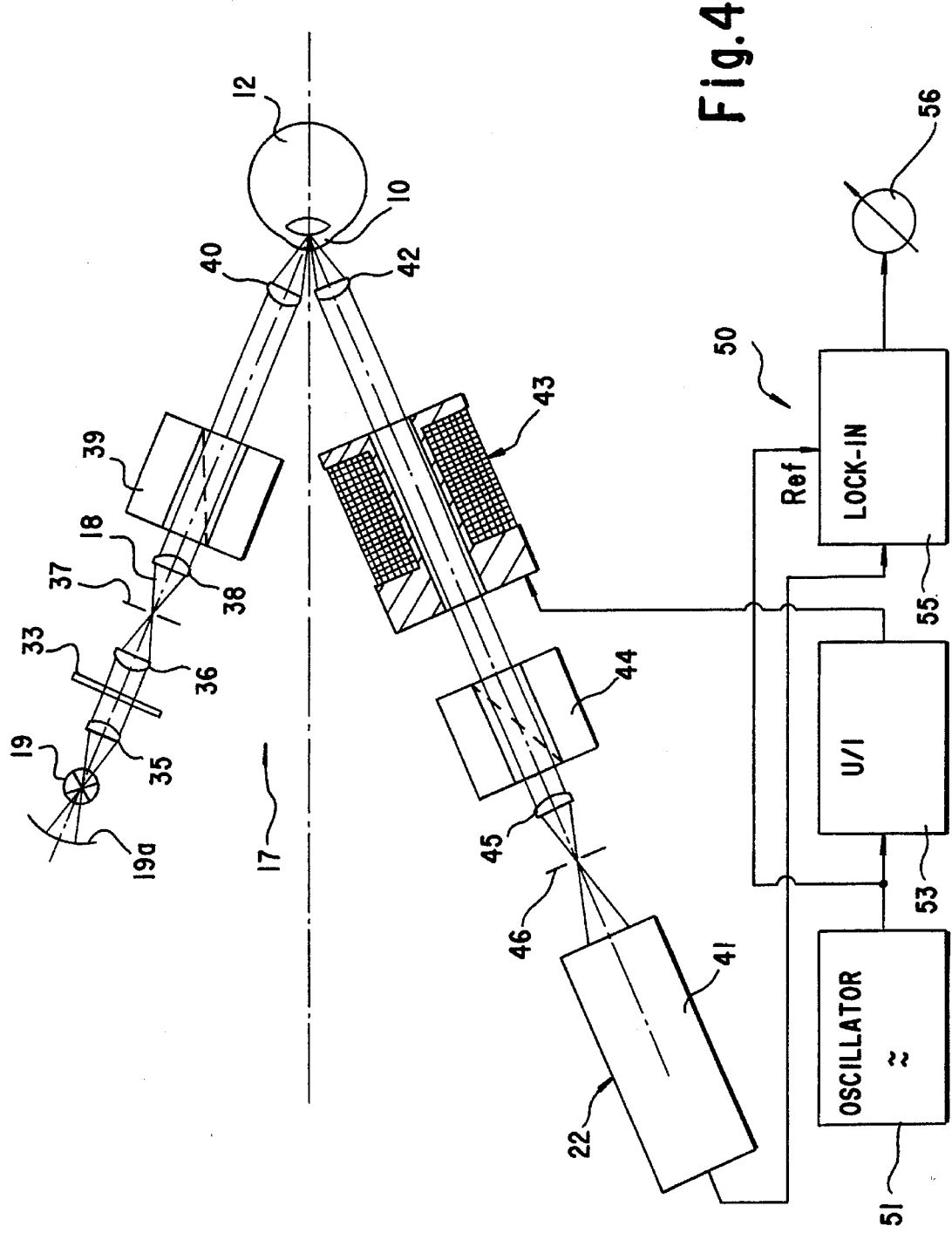
FIG. 4 shows an overall view of an alternative embodiment of a device according to the invention with a signal processing unit for the determination of the optical rotation.

FIG. 4 shows an embodiment with which the optical rotation dependent on the glucose concentration in the aqueous humour 10a may be determined. This embodiment is also only an example; other signal processing units may be used for determining the optical rotation, such as are known from the literature mentioned in the preamble.

The primary-side light path 18 of the optical unit 17, which issues from a light source 19 with a concave mirror 19a, leads through a first plano-convex lens 35, a filter 33, a second plano-convex lens 36, an iris diaphragm 37, a third plano-convex lens 38, a polarizer 39 and a fourth plano-convex lens 40 into the anterior chamber 10 of an eye 12. The detector 22 is in the case shown constructed as a photomultiplier 41. The secondary-side light path leading from the anterior chamber 10 to the photomultiplier 41 passes through a fifth plano-convex lens 42, a Faraday modulator 43, a second polarizer 44 serving as an analyzer, a sixth plano-convex lens 45 and a second iris diaphragm 46. The Faraday modulator 43 and the photomultiplier 41 are connected to the signal processing unit designated overall as 50.

The operation ot the device shown in FIG. 4 will be discussed below:

The light generated by the light source 19 should have its maximum wavelength as far as possible in the desired wavelength range. In the case of the reflection measurement according to the invention use will be made, in contrast to previously known methods, preferably of relatively short wavelengths in the blue region of visible light or in the UV region, as the optical rotation increases with the movement towards short wavelengths. The radiated noise is admittedly also stronger for light in the blue region than in the red. The radiated noise can, however, be suppressed better in the case of the light path concept according to the invention than in the case of previously known arrangements.

A suitable light source is constituted in particular by a laser or a laser diode, if the latter is available in the desired wavelength range at justifiable cost. Another light source, for example—as shown—an iodine-quartz lamp, is however also suitable. The light issuing from the light source 19 is imaged through the lenses 35, 36 onto the diaphragm 37 and filtered simultaneously through the filter 33. The passband wavelength of the filter preferably is between 290 nm and 440 nm. The lenses 38 and 40 form, together with the lenses 35 and 36, an optical imaging system, by means of which the light source 19 is imaged onto the reflecting interface on the rear side of the anterior chamber 10. Between the lenses 38 and 40 the light path is largely parallel. A linear polarization by means of the polarizer 39 takes place here. Since the transmission of the usual polarization films is too small in the UV, polarizing prisms are used for the polarizer 39 as well as for the analyzer 44.

In the secondary-side light path 20 there is also located between the lenses 42 and 45 a section with a substantially parallel light path, in which, in addition to the manually or electrically rotatable analyzer 44, the Faraday modulator 43 is disposed. The function of a Faraday modulator is based on an optical rotation effect which many materials exhibit when they are traversed by a magnetic field, with the beam direction running parallel to the magnetic field lines. The magnitude of the effect is determined by a material constant, the so-called Verdet constant. If such a material is placed in a coil through which an electric current flows, the strength and direction of the optical rotation can be adjusted by variation of the current.

In the present case the Faraday modulator 43 serves to modulate the polarization direction of the light beam. To this end the analysis unit 50 comprises an oscillator 51 which generates a sinusoidal signal that is passed to a voltage-current transducer 53. The latter feeds the Faraday modulator with a current which is proportional to its input signal.

Figure 5:
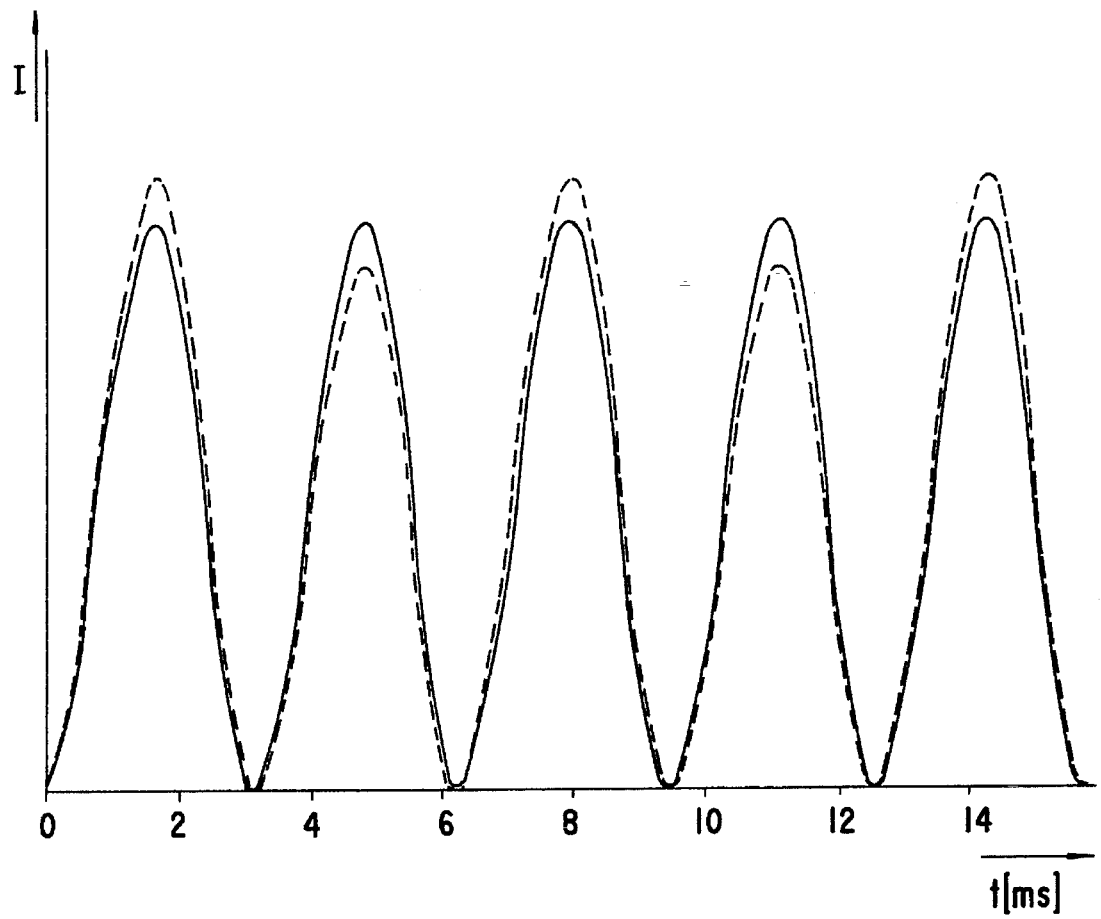
FIG. 5 shows a graph of a detector signal for the embodiment of FIG. 4.

FIG. 5 shows the plot, measured by the detector 22, of the signal I for the case where the analyzer is oriented perpendicularly to the polarization plane of the polarizer (dark position). The periodic modulation by the Faraday modulator 43 with a frequency f results in luminosity maxima with a frequency 2f occurring behind the analyzer 44. The solid line of FIG. 5 shows the signal plot without including the optical rotation produced by the glucose.

The modulation frequency f is therefore contained in the signal recorded by the detector 22. The signal may be specifically recorded and amplified by means of a lock-in amplifier. To this end the frequency of the oscillator 51 is passed to the reference input of the lock-in amplifier 55.

The optical rotation caused by glucose in the anterior chamber 10 results in the successive luminosity maxima caused by the modulation no longer being the same size (FIG. 5, dotted line). The lock-in amplifier generates an output signal correlating with the difference of the luminosity maxima and hence with the optical rotation due to the glucose, which may be displayed on a monitor 56 or processed further in the usual manner. The zero point can be adjusted by means of a surface positioned in the area of the eye lens, said surface having a similar reflectance to that of the interface 23, but causing no optical rotation.

The embodiment described above with reference to FIGS. 2 and 3 of an electronic analysis unit suitable for the invention with the use of a Faraday modulator is particularly preferred, as no moving parts are necessary and only one Faraday modulator is required. It is therefore particularly suitable for relatively simply constructed reliable units such as a diabetic requires for the routine checking of his glucose levels. In principle, however, other measuring technology procedures with which very small optical rotations may be recorded are also suitable, such as are explained in detail for example in the literature references mentioned before.

We claim:

1. An apparatus for in vivo determination of an optical property of an aqueous humour in an anterior chamber of a patient's eye, said apparatus comprising:

an optical unit;

a light source fixed to said optical unit for irradiating light along a primary-side light path into the anterior chamber, said primary-side light path having a central ray;

a detector fixed to said optical unit for detecting light originating from said light source and issuing from said anterior chamber along a secondary-side light path, and generating a measured signal representative of detected light, said secondary-side light path having a central ray; and signal processing means coupled to said detector, said signal processing means for determining optical properties of the aqueous humor based upon said measured signal, wherein said optical unit is configured to be positioned in front of the patient's eye, such that said optical unit directs said primary side light path to a partial area of a front interface of a lens of the eye and said central rays of said primary-side light path and said secondary-side light path are disposed to be at equal and opposite angles from a normal to the front interface of the lens whereby specular reflection from the interface is detected by the detector.

2. An apparatus as recited in claim 1, wherein said optical unit further directs said primary side light path to the partial area of the front interface in a vicinity of an optical axis of the eye in front of a pupil of the patient's eye.

3. An apparatus as recited in claim 2, further comprising an optical imaging system disposed in said secondary-side light path, said optical imaging system generating an image of the interface on the detector.

4. An apparatus as recited in claim 3, wherein said optical imaging system comprises restriction means adapted to be disposed between the patient's eye and said detector, for restricting specularly reflected light of said secondary-side light path to a predetermined portion of the interface.

5. An apparatus as recited in claim 4, wherein means are provided for restricting the primary side light path to selectively illuminate the predetermined portion of the interface to which the secondary-side light path is limited.

6. An apparatus as recited in claim 1, further comprising face mask means having said light source and said detector incorporated therein, said face mask means for individually fitting the apparatus to a face of a patient, said face mask means including means to locate the light source and the detector in a defined position with respect to the patient's eye.

7. An apparatus as recited in claim 1, wherein said signal processing means determines optical rotation based upon the measured signal of the detector.

8. An apparatus as recited in claim 7, wherein said light irradiated from said light source into the anterior chamber has a wavelength between 290 nm and 400 nm.

9. An apparatus as recited in claim 1, wherein an optical property determined by the signal processing means is optical absorption.

10. An apparatus as recited in claim 9, wherein said optical absorption is optical absorption in a near infrared range.

11. An apparatus as recited in claim 1, wherein said optical properties determined by said signal processing means are optical rotation and optical absorption.

12. A method for in vivo determination of an optical property of an aqueous humour in an anterior chamber of a patient's eye, said method comprising the steps of:

providing a light source and a detector, said light source providing a primary-side light path having a central beam;

positioning said light source and said detector in front of the patient's eye, wherein the central beam of the primary-side light path and a central beam of a secondary-side light path each form an acute angle with respect to a respective normal to a surface of a cornea of the eye;

irradiating light from the light source along the primary-side light path into the anterior chamber of the eye;

detecting light originating from said light source and issuing from said anterior chamber along the secondary-side light path;

generating a measuring signal representative of said detected light;

determining optical properties based upon said measured signal, wherein said detected light is reflected from a front interface of a lens of the eye.

* * * * *